United States Patent [19]

Bourque

[11] Patent Number: 5,163,940

[45] Date of Patent: Nov. 17, 1992

[54] SURGICAL DRILL GUIDE FOR TIBIA

[75] Inventor: Bernard J. Bourque, Taunton, Mass.

[73] Assignee: American Cyanamid Company, Stamford, Conn.

[21] Appl. No.: 664,597

[22] Filed: Mar. 4, 1991

[51] Int. Cl.⁵ .............................................. A61F 5/04
[52] U.S. Cl. ..................................... 606/96; 606/88; 606/103
[58] Field of Search ............... 606/103, 80, 75, 73, 606/96, 88, 63, 99, 97, 98, 108

[56] References Cited

U.S. PATENT DOCUMENTS

| | | | |
|---|---|---|---|
| 4,672,957 | 6/1987 | Hourahane | 606/96 |
| 4,781,181 | 11/1988 | Tanguy | 606/80 |
| 4,860,742 | 8/1989 | Park | 128/772 |
| 4,883,048 | 11/1989 | Purnell | 606/96 |
| 4,920,958 | 5/1990 | Walt | 606/96 |
| 4,922,897 | 5/1990 | Sapega | 606/73 |

FOREIGN PATENT DOCUMENTS

| | | | |
|---|---|---|---|
| 2747568 | 4/1979 | Fed. Rep. of Germany | 606/80 |
| 921543 | 4/1982 | U.S.S.R. | 606/96 |
| 1109144 | 8/1984 | U.S.S.R. | 606/96 |

*Primary Examiner*—Robert A. Hafer
*Assistant Examiner*—David J. Kenealy
*Attorney, Agent, or Firm*—Douglas E. Denninger

[57] ABSTRACT

The invention comprises arcuate support beam (22) having a drill guide locator (24) and locator probe (28) mounted thereon. The drill guide locator (24) is adapted to hold a cannulated drill sleeve (32) by means of a sleeve locking mechanism (26). The sleeve locking mechanism (26) comprises cam surface trigger lock with an inclined surface (168) and biased plunger member (174, 176). The locator probe (28) is held in place on the support beam (22) by a probe locking mechanism (30). The mechanism (30) has teeth (122) which mate in locking engagement with a series of ribs (40) on the beam (22). Spring biased pins (124) keep the mechanism (30) from engaging the ribs (40) in the unlocked condition.

27 Claims, 4 Drawing Sheets

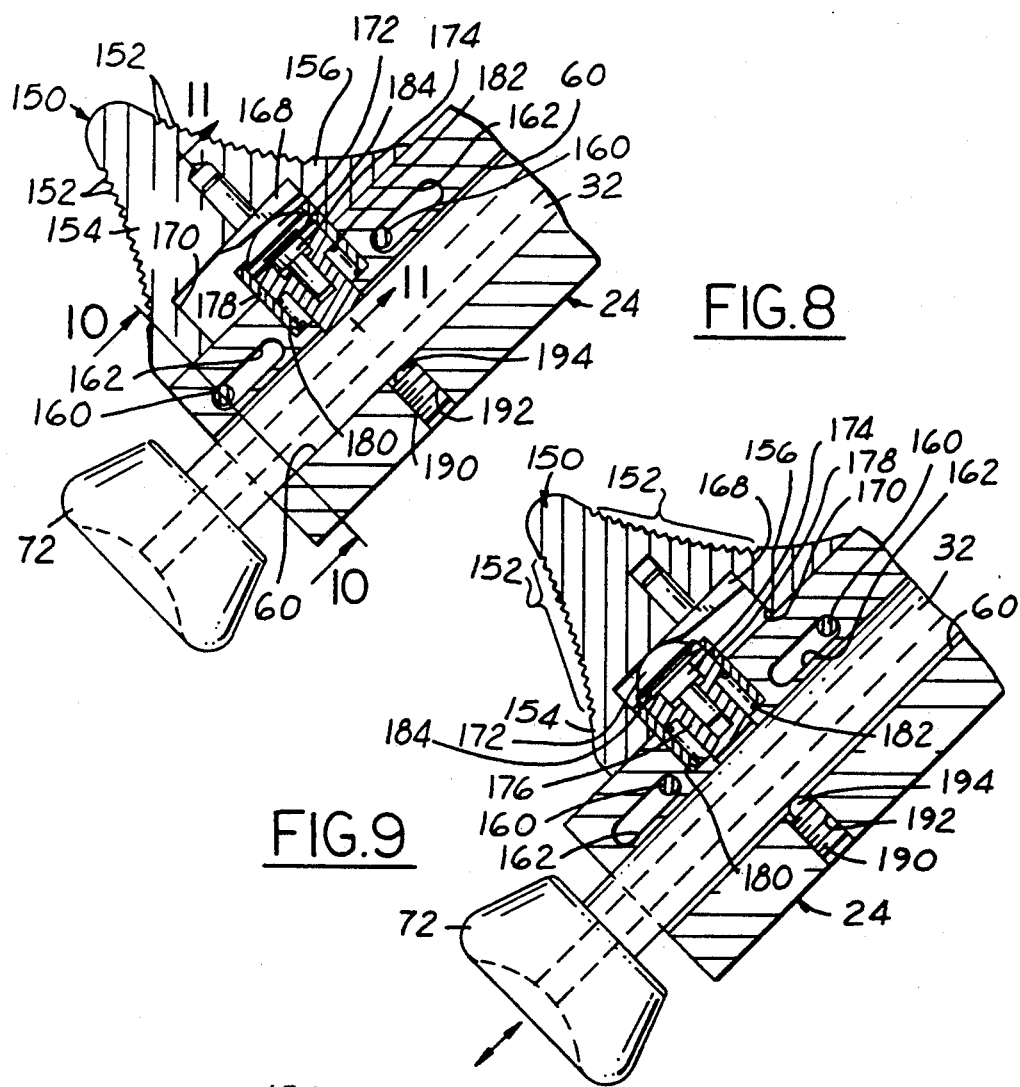

SURGICAL DRILL GUIDE FOR TIBIA

TECHNICAL FIELD

The present invention relates generally to devices used in arthroscopic surgery for positioning and guiding drills used to form passages in bone. More particularly, the invention is directed to surgical apparatus and methods used in the reconstruction of anterior cruciate ligaments in the human knee.

BACKGROUND ART

The anterior and posterior cruciate ligaments in the knee act in conjunction with the other ligaments and soft tissue to provide both static and dynamic stability to the function of the knee. Often for example, due to sports related injuries, the anterior cruciate ligament (ACL) becomes ruptured or torn. This requires replacement and reconstruction of the ligament in order to restore normal usage of the knee.

When the ACL is replaced, a substitute synthetic or harvested graft is typically utilized. The graft is anchored in place either inside or outside tunnels or passages formed in the tibia and femur. The operation and interdependency of the ACL with the other knee ligaments, bones and soft tissue is complex and for optimum reconstruction much precision is required in the formation and positioning of the passageways for the substitute graft, as well as in the methods and mechanisms used to anchor the graft. For best performance of the knee joint after surgery, it is necessary to locate and drill the tunnels at precise isometric locations so the graft will be implanted in the optimum position.

A drill guide for locating the precise tibial tunnel location and accurately aiming the tunnel forming drill is an important part of a successful ACL reconstruction procedure. The guide should have a probe or locator tip, as well as a drill jig or sleeve, at least one of which should be adjustable in order to accommodate differently sized and shaped human knees. The adjustable feature should also be quickly and accurately locked or otherwise held in position.

Once the guide device is properly positioned, a thin wire drill is first installed to mark and locate the passageway. After the guide device is removed, a cannulated surgical drill is used to form the complete passageway in the tibea. Thereafter, tibial tunnel or rear entry techniques are used to form the femoral tunnel and complete the ligament reconstruction procedure.

Other drill guide devices used in arthroscopic surgery are shown, for example, in U. S. Pat. No. 4,672,957 to Hourahane, No. 4,781,182 to Purnell et al., No. 4,920,958 to Walt et al. and No. 4,883,048 to Purnell et al. Additional surgical devices are shown in the two Sapega et al. U.S. Pat. Nos. 4,739,751 and 4,922,897. Another known device is the "Bow & Arrow" drill guide made by Instrument Makar in Okemos, Mich.

It is an object of the present invention to provide a method and apparatus for the proper and accurate location and placement of replacement graft passages in ACL reconstruction operations.

It is another object of the present invention to provide an improved tibial tunnel placement guide for use in knee surgery. It is still another object to provide a unique surgical tunnel placement guide which is easier to operate and more accurate and precise than guides known in the field.

It is a further object of the invention to provide a tibial drilling device with improved locking and securing mechanisms for positioning of the location probe and for holding of the wire drill guide sleeve.

Additional objects, advantages, and novel features of the invention are set forth in the description of the invention contained in this document which will be understood by persons skilled in the art upon examination of the following description and accompanying drawings or may be learned by practice of the invention. The objects and advantages of the invention may be realized and obtained by means of the instrumentalities and combinations particularly pointed out in the appended claims.

DISCLOSURE OF INVENTION

The present invention provides improved apparatus and method for assisting in the reconstruction of ACLs in human knees. The invention facilitates the implanting of the graft at the isometric points of origin for the ACL.

The device of the preferred embodiment of the invention comprises an arcuate beam or support means having a series of ribs along the curved outer surface. A channel is located on the curved inner surface of the beam. A drill guide locator is integrally formed at one end of the support beam. A cannulated drill sleeve is positioned in the locator and releasably held in place by a unique locking mechanism. The locking mechanism has a cam surface trigger lock which holds the sleeve in position.

A locator probe is also positioned on the curved beam. The probe has a bent elongated shaft ending in a locator tip which is positioned on the ACL origin site by the surgeon. A unique releasable locking mechanism is used to hold the probe at the desired position on the beam. The probe locking mechanism has a turn knob which when rotated loosens or tightens spring biased members which are adapted to mesh or mate with the ribs on the outer surface of the beam.

Due to the curvature of the beam, a drill positioned through the drill sleeve held in the locator will be automatically aimed adjacent the end of the probe locator tip.

In the operation of the invention, the tip of the locator probe is arthroscopically located at the desired position (ACL tibial origin site) by the surgeon. A cannulated drill sleeve is positioned in the drill guide locator and secured in place by the sleeve locking mechanism. The locator probe is adjusted if necessary along the beam by use of the probe locking mechanism and locked securely in place. The drill sleeve is also adjusted in the drill guide locator so its point contacts the tibia. Tightening of the sleeve locking mechanism locks the entire drill guide apparatus into one rigid structure.

A thin wire drill is inserted through the drill sleeve and drilled into and through the tibea. The sleeve locking mechanism is then released and the drill sleeve is removed leaving the wire drill in place. The drill guide apparatus is subsequently removed entirely from the surgical site and a cannulated surgical drill is used to form the tibial tunnel or passageway using the installed wire drill as a guide.

The completion of the ACL reconstruction procedure is carried out by conventional procedures.

BRIEF DESCRIPTION OF THE DRAWINGS

FIG. 8 is an enlarged cross-sectional view of the unique locking mechanism for the drill guide sleeve shown in the locked position;

FIG. 9 is an enlarged cross-sectional view of the unique locking mechanism for the drill guide sleeve shown in the unlocked position;

FIG. 10 is a cross-sectional view of the drill guide locking mechanism taken along line 10—10 in FIG. 8;

FIG. 11 is a cross-sectional view of the drill guide locking mechanism taken along line 11—11 in FIG. 8.

BEST MODE(S) FOR CARRYING OUT THE INVENTION

Figures 1, 2:
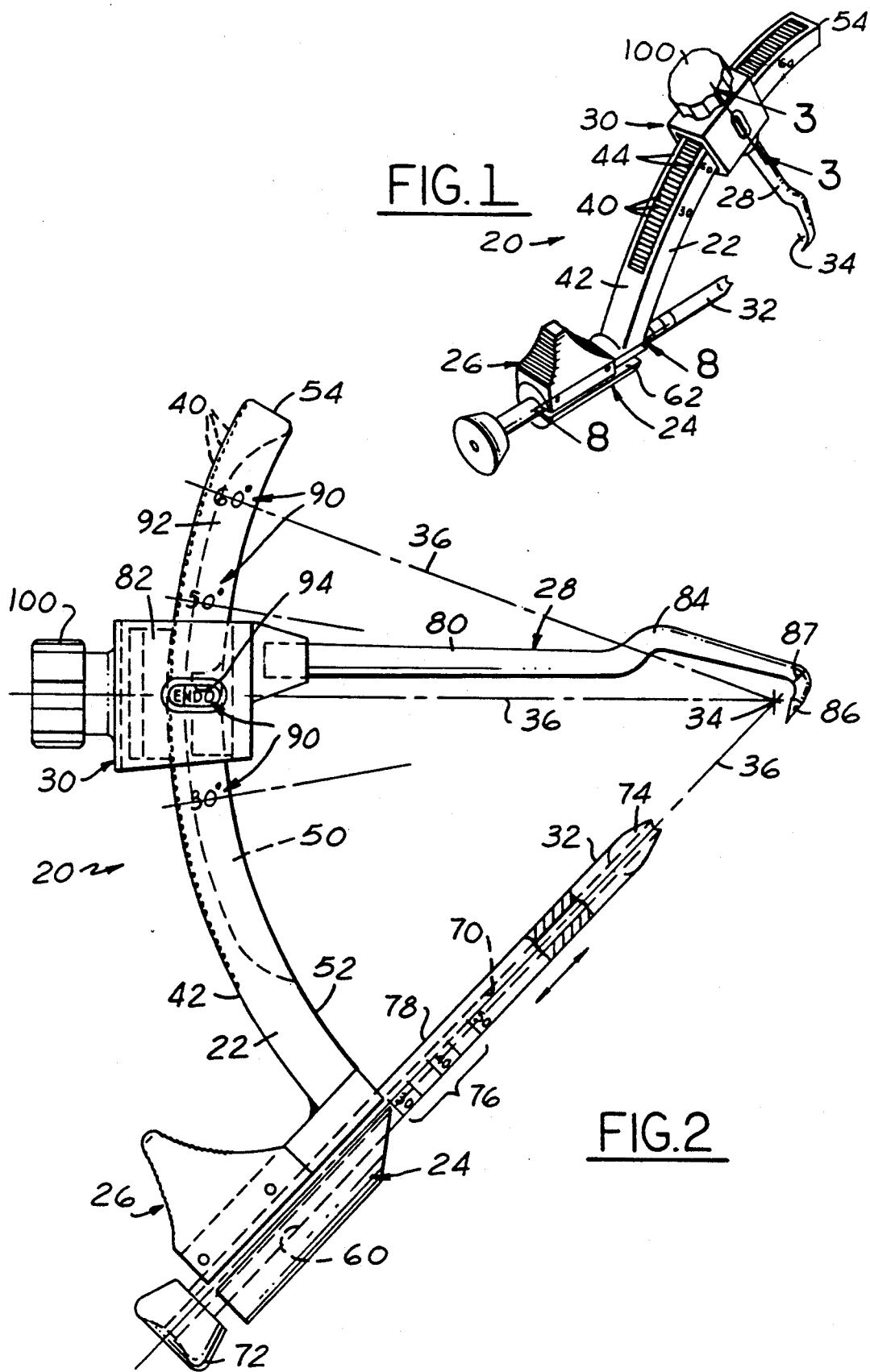
FIG. 1 is a perspective view of the preferred embodiment of the invention.
FIG. 2 is a side elevational view of the invention device.

The inventive drill guide device 20 is shown in FIGS. 1 and 2. FIG. 1 shows the device 20 in a perspective view while FIG. 2 is a side view of the device.

The device 20 has a curved beam or support 22, a drill guide locator 24, a sleeve locking mechanism 26, a locator probe 28, and a probe locking mechanism 30. A drill sleeve 32 (also called a "bullet") is also provided.

The beam 22 is arcuate in shape; it has a curvature which defines part of the perimeter of a circle. As shown in FIG. 2, the curvature of the beam has a center point 34. The arcuate shape of the beam assures that the end of the locator probe 28 and a drill positioned in the drill guide locator 24 will have a common point of intersection (at or adjacent point 34) regardless of the position of the locator probe 28 along the beam 22.

The curved beam 22 has a generally rectangular cross-section. A series of ribs or "teeth" 40 are provided along the outer curved surface 42 of the beam 22. The ribs 40 are recessed in an elongated channel below the surface of the beam 22. A pair of outer ridges or tracks 44 are provided on the outer surface 42 of the beam 22 along the two sides of the elongated series of ribs 40. The ribs and tracks facilitate the ability of the probe locking mechanism 30 to lock and secure the locator probe 28 at any desired point along the beam 22 (as described in more detail below).

A channel 50 is located along the inner curved surface 52 of the beam 22. The channel 50 begins near a first end 54 of the beam 22 and extends for the majority of the length of the beam. The channel 50 facilitates the positioning and sliding adjustability of the locator probe 28 along the beam, also as described in more detail below.

The drill guide locator 24 is integrally formed on the end of the beam 22 opposite the first end 54. It is permanently formed and affixed to the beam; it is not slidable or movable relative to it. The drill guide locator 24 has a circular cross-section and a longitudinally extending channel or passageway 60 for holding the drill sleeve or bullet 32. The channel 60 has a slit 62 along its entire length for passage of a wire drill, as described below. The width of the slit 62 should be sufficient to allow passage therethrough of thin wire drills (also known as "K-wires") conventionally used in reconstructive knee surgery.

The drill sleeve 32 is cannulated; it has a longitudinal passageway 70 for holding and guiding a wire drill. The drill sleeve also has an enlarged head 72 at one end and a sharp tri-point tip 74 at the other end. A scale or series of markings 76 are preferably provided on the outer surface of the barrel or body 78 of the drill sleeve. The unit measurements of the scale are in millimeters and are used by the surgeons to accurately position the drill sleeve in the drill guide locator 24.

The locator probe 28 comprises an elongated shaft 80 which is rigidly affixed to a probe housing 82. The shaft 80 is bent or curved in the manner shown at 84 (FIG. 2) in order to allow the probe to be inserted and positioned in the knee joint without contacting or being interfered with by the tibial plateau or the patella. The tip 86 of the probe is angled approximately 90° to the shaft 80 and has a sharp point. A line 87 is laser etched at the elbow between the tip and the shaft.

The beam 22 has a series of angularity markings 90 on one or both of its side surfaces 92. The probe housing 82 has one or more openings 94 which are positioned to allow viewing of the markings 90 through it. The markings 90 allow the surgeon to position the probe 28 at prespecified or desired locations on the beam 22.

The details of the probe locking mechanism 30 are shown in FIGS. 3-7. The locking mechanism is manually operated by knurled knob 100 which has a threaded shaft 102. The shaft 102 extends into a mating threaded socket 104 in the probe housing 82. The end 106 of shaft 102 fits within opening 108 in endplate 110 and rests against the upper surface 112 of lockplate 114. The endplate 110 is attached to the lockplate 114 by a pair of screws 116.

The lockplate 114 has four stepped bores 120 and a pair of lock teeth 122. Slide pins 124 biased by compression coil springs 126 are positioned in each of the four bores 120. The pins and springs are held in place by endplate 110; the force of the springs 126 normally pushes the ends of the pins 124 past the lower surface 128 of the lockplate 114 (see FIG. 4).

Figure 3:
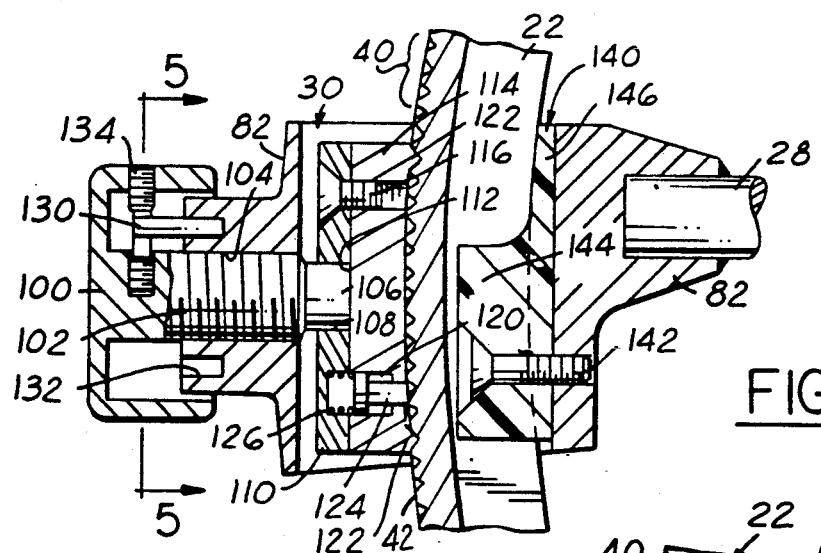
FIG. 3 is an enlarged cross-sectional view of the unique locking mechanism for the locator probe shown in the locked position.
Figures 4, 5:
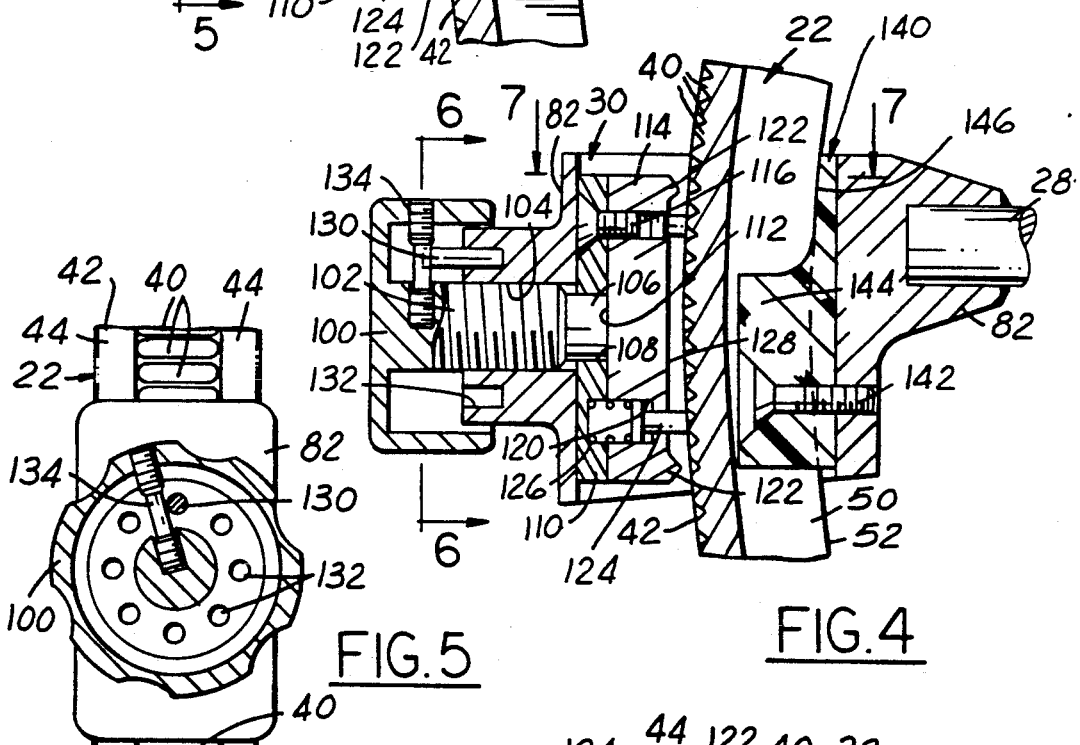
FIG. 4 is an enlarged cross-sectional view of the unique locking mechanism for the locator probe shown in the unlocked position.
FIG. 5 is a cross-sectional view of the turn knob of the probe locking mechanism taken along line 5—5 in FIG. 3.
Figures 6, 7:
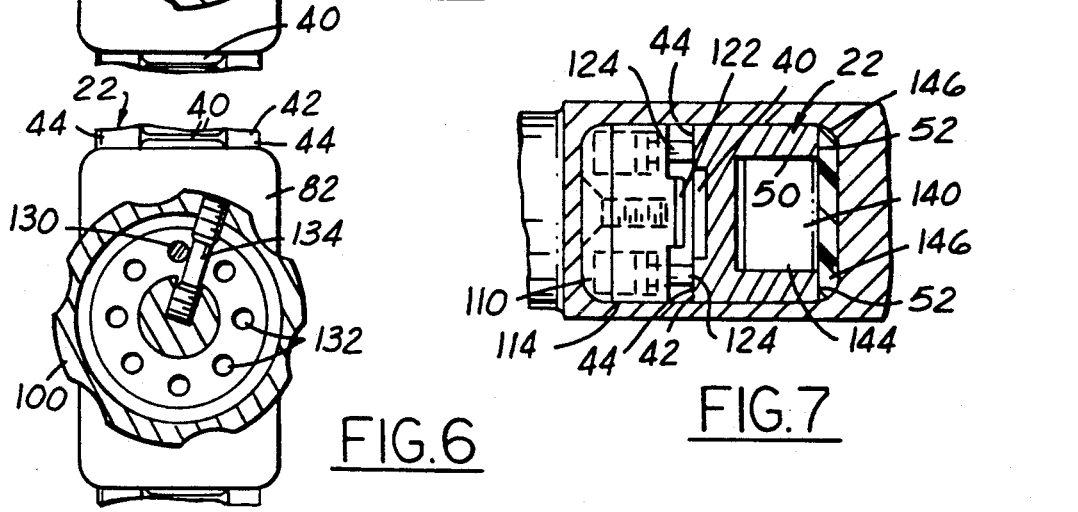
FIG. 6 is a cross-sectional view of the turn knob of the probe locking mechanism taken along line 6—6 in FIG. 4.
FIG. 7 is a cross-sectional view of the probe locking mechanism taken along line 7—7 in FIG. 4.

As shown in FIGS. 3 and 4, the operation (rotation) of the knob 100 in a clockwise direction forces the end 106 of the shaft 102 against the endplate and lockplate and in turn forces the lock teeth 122 into engagement with the ribs or teeth 40 on the support beam 22. Rotation of the knob overcomes the biasing force of the springs 126 forcing the slide pins 124 to be retracted into the lockplate. This securely locks the locator probe 28 in place on the beam 22 at that position (see FIG. 3).

To release the locking mechanism 30 and thus adjust the position of the locator probe 28 relative to the beam 22, the knob 100 is rotated in the opposite direction (i.e. counterclockwise). This allows the springs 126 to push the pins 124 against the curved tracks 44 on the outer surface 42 of the beam 22 and thus disengages the lock teeth 122 from the ribs 40. When the locking mechanism 30 is disengaged (i.e. unlocked) in this manner, the locator probe 28 can be slid along the beam, with the pins 124 sliding along the tracks 44.

The knob 100 is attached to the housing 82 in a manner such that it cannot be removed, and also so that slightly less than one 360° revolution will allow the full engagement and disengagement of the locking teeth (and thus locking or unlocking of the probe 28). A roll pin 130 is press fit in one of the series of openings 132 provided in the housing 82. (The precise location of the roll pin is ascertained after the device 20 is initially assembled and a determination is made as to the optimum arc of rotation of the knob 100.) Once the knob 100 is secured into place, a set screw 134 threaded at both ends is positioned in it. The set screw 134 acts as a stop (in combination with the roll pin 130) to prevent rotation of the knob more than 360° and at the same time prevents removal of the knob from the housing 82.

A slide 140 is also part of the housing 82. The slide 140 is positioned in the channel 50 in the beam 22 and is connected by screw 142 to the housing 82. The slide has a main body 144 which fits within the channel 50 and a pair of curved flange members 146 which rest and slide on the curved inner surface of the beam alongside the channel 50. The slide 140 is made from a reduced friction material, such as Delrin, and allows the locator probe 28 to move and slide more easily along the beam 22 when it is being adjusted. The slide 140 also acts in cooperation with the lockplate 114 to clamp the housing 82 to the beam when the locking mechanism 30 is engaged (i.e. locked).

The sleeve locking mechanism 26 is shown in detail in FIGS. 8-11. The locking mechanism generally comprises a trigger-type slide lock which has a cam action to frictionally hold the drill guide sleeve 32 in place in the drill guide locator 24.

The mechanism 26 has a latch housing 150 which has a series of ridges or ribs 152 on its outer surfaces 154, 156 to optimize manual operation. The housing 150 is held onto the drill guide locator 24 by a pair of glide pins 160. The pins fit within slots 162 in the locator 24 and are threaded into threaded bores 164 in the housing 150. (A slot head for a small screwdriver or other tool is provided on one of the ends of each glide pin for ease of installation.) The slots 162 allow the latch housing 150 to move laterally or slide along the locator 24 (compare FIGS. 8 and 9).

Angled or inclined cam surface 168 is positioned (press fit) in chamber 170 in latch housing 150. The cam surface 168 is positioned to make contact with the head 172 of plunger pin 174 when the housing 150 is moved along the drill guide locator 24.

The plunger pin 174 is positioned in pin housing 176 in locator 24. The housing 176 is slidingly assembled in cylindrical bushing 178 which in turn is mounted in stepped bore 180.

Compression coil spring 182 biases the pin housing 176 relative to the drill guide locator 24. A pair of spring washers 184 (e.g. Belleville washers) are used to bias the head 172 of the plunger pin 172 relative to the pin housing 176. The spring washers preload the plunger pin and prevent the head of the pin from scoring the chamber 170 or cam surface 168.

When the sleeve locking mechanism 26 is operated, the latch housing 150 is manually moved between the two positions shown in FIG. 8 (locked) and FIG. 9 (unlocked). When the mechanism 26 is locked, the housing 150 is slid to the left (as shown in FIG. 8) which forces the cam surface 168 against the plunger pin and in turn the pin housing 176 against the sleeve 32 positioned in the drill guide locator. When the mechanism is unlocked, the situation is reversed. The housing 150 is slid to the right (FIG. 9) which allows the spring 182 to withdraw the pin housing 176 from contact with the sleeve 32 and thus release the sleeve.

A spring plunger 190 (such as a Valier "ball plunger") is positioned in a bore 192 in the drill guide locator 26. The plunger 190 has a nylon ball 194 in one end which protrudes beyond the surface of the passageway 60 in the locator 24 (see FIG. 9). The plunger 190 provides a sufficient amount of force on the sleeve in the locator passageway to prevent it from being dislodged or falling out when the device 20 is moved or utilized while the locking mechanism 26 is unlocked. The biasing force on the ball 194 is also sufficiently small so that it is easily overcome when the latch housing is slid over to lock the sleeve in place.

Figure 12:
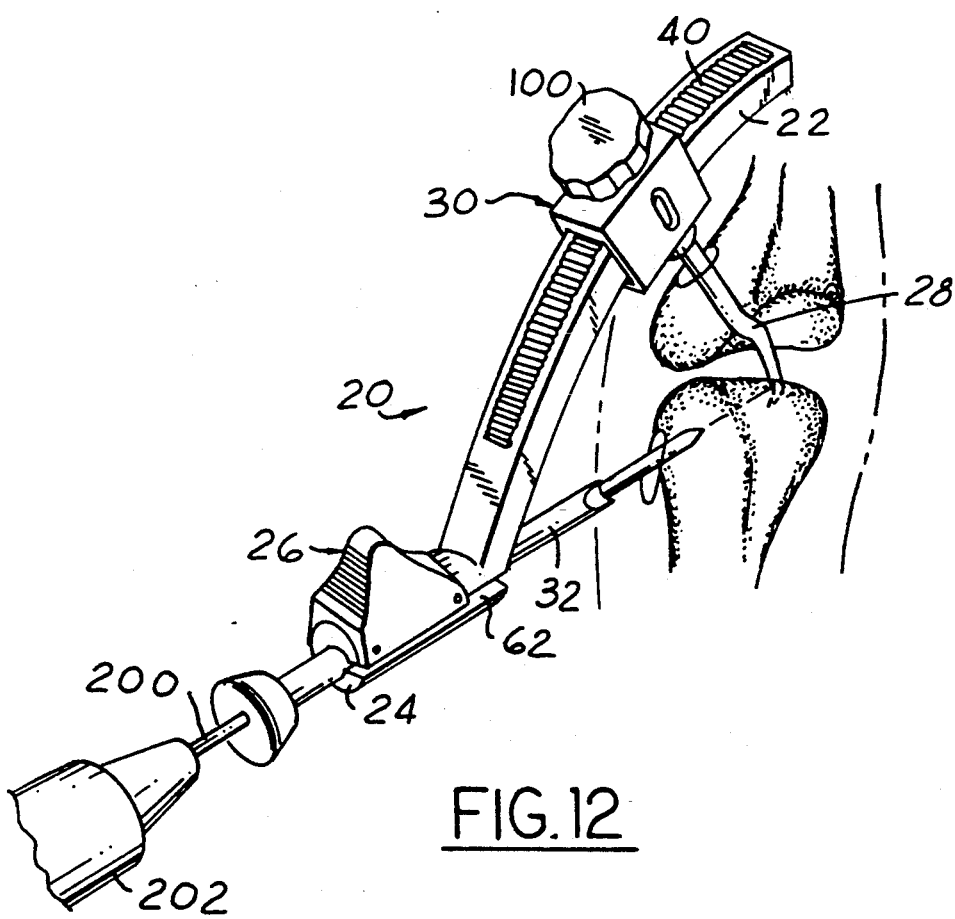
FIG. 12 is a perspective view illustrating the use of the present invention.

The use of the inventive instrument 20 in ACL reconstructive surgery is shown in FIG. 12. After the portals are formed, the knee is examined arthroscopically and minor damage repaired, the device 20 is prepared for use. The probe locking mechanism is initially locked in place in the approximate position preferred by the surgeon or dictated by the patient's knee.

The locator probe is then inserted into the knee joint and the tip 86 is firmly held in place at the ACL origin site. The bullet sleeve 32 is positioned in the locator 24 and adjusted in position. The locking mechanism 30 can also be released and the probe adjusted again if desired by the surgeon. Once the bullet tip 74 is positioned on the tibea at the site selected by the surgeon, the sleeve locking mechanism is locked. This produces a rigid assembly.

A thin wire drill 200 is positioned through the bullet sleeve and drilled into the tibea with a conventional motorized drill 202. Once the thin wire drill 200 is installed in place, the device 20 is removed. First the locking mechanism 26 is unlocked and the bullet sleeve 32 removed. Then the device 20 is detached from the wire (by passing the wire 200 through the slot 62), the probe 38 is removed from the knee joint.

With the guide wire 200 set in place in its proper position, a cannulated drill (not shown) is utilized to finish the tibial tunnel. The remainder of the ACL reconstruction procedure is then followed in accordance with the desires of the surgeon.

Preferably, the parts of the device are made of strong, durable materials which are auto-clavable. Most of the parts are preferably made of stainless steel, for example, 17-4 and 400-series stainless steel. These parts include the beam 22 and drill guide locator 24, the locator probe 28 and the drill guide sleeve 32, as well as many of the internal parts for the two locking mechanisms 26 and 30. Certain portions are also preferably coated with titanium nitride, such as the drill sleeve 32 and the locator probe 28 (including the shaft and housing). This adds additional hardness as well as lubricity to the parts. The slide 140 is preferably made of Delrin black (500 series), and the pin housing is made of brass. The end plate 110, knob 100, and latch housing 150 are made of aluminum (6061-T651). The aluminum is preferably coated with an anti-oxidation material.

Although particular embodiments of the present invention have been illustrated in the accompanying drawings and described in the foregoing detailed description, it is to be understood that the present invention is not to be limited to just the embodiments disclosed, but that they are capable of numerous rearrangements, modifications and substitutions without departing from the scope of the claims hereafter.

It is claimed:

1. A device used to position and guide drills for forming bone passages during surgery, said device comprising:
   a) a support member;
   b) a drill guide locator member positioned on said support member;
   c) a first locking mechanism on said drill guide locator member for securing a drill sleeve member therein;
   d) a locator probe member positioned on said support member;
   e) a second locking mechanism on said locator probe member for securing said probe member to said support member; and
   f) said first locking mechanism having an inclined surface and a biased plunger member, and further including a manually actuable housing member slidably mounted on said drill guide locator member and carrying one of said inclined surface and said biased plunger member, the other of said inclined surface and said biased plunger member being separately mounted on said drill guide locator member, whereby actuation of said housing member moves said inclined surface relative to said biased plunger member.

2. The device of claim 1 wherein said housing member carries said inclined surface, and actuation in a first direction drives said biased plunger member into locking contact with the drill sleeve member to secure it in place.

3. The device of claim 2 wherein subsequent actuation of said housing member in a second, opposite direction enables said biased plunger member to withdraw from the drill sleeve member.

4. The device of claim 3 further including biased retention means, carried by said drill guide locator member, for releasably holding the drill sleeve member in place when said biased plunger member is withdrawn from locking contact with the drill sleeve member.

5. The device of claim 4 wherein said biased retention means includes a ball plunger member disposed in said drill guide locator member and having a biased ball means for slidably contacting the drill sleeve member, said biased ball means releasably retaining the drill sleeve member in place.

6. The device of claim 1 wherein said support member comprises an arcuate beam.

7. The device of claim 1 wherein said support member has first teeth means thereon and said second locking mechanism has second teeth means which mate with said first teeth means to securely hold said probe member in position on said support member when said second locking mechanism is moved to its locked position.

8. The device of claim 7 wherein said second locking mechanism includes a lockplate member carrying said second teeth means and having at least one biased element for slidably contacting said support member, said biased element resisting engagement between said first and second teeth means when said second locking mechanism is moved to its unlocked position.

9. The device of claim 8 wherein said support member defies at least two smooth tracks extending along said first teeth means, and said lockplate member includes at least one biased element for contacting and travelling along each said track.

10. The device of claim 8 wherein said second locking mechanism further includes a threaded turn knob for selectively contacting said lockplate member to engage said first and second teeth means when rotated in a first direction and for disengaging said first and second teeth means when rotated in a second direction.

11. The device of claim 7 wherein said locator probe includes a low-friction glide member for slidably contacting said support member to assist adjustment in position of said locator probe.

12. The device of claim 11 wherein said support member defines said first teeth means on a first surface and further defines a channel along a second surface, and said glide member extends into and travels along said channel.

13. The device of claim 1 wherein said drill guide locator member defines a slit extending along its length for removing a narrow-diameter drill laterally from the interior of said drill guide locator member.

14. A device used to position and guide drills for forming bone passages during surgery, said device comprising:
   a support member;
   a drill sleeve member having a passage for receiving a drill therethrough;
   a drill guide locator member positioned on said support member for slidably carrying said drill sleeve member;
   a first locking mechanism on said drill guide locator member for securing said drill sleeve member therein when said first locking mechanism is in a locked position; and
   biased retention means, carried by said drill guide locator member, for releasably holding said drill sleeve member in place when said first locking mechanism is in an unlocked position, said biased retention means including a ball plunger member disposed in said drill guide locator member and having a biased ball means for slidably contacting the drill sleeve member, said biased ball means releasably retaining the drill sleeve member in place.

15. The device of claim 14 wherein said drill guide locator member defines a slit extending along its length for removing a narrow-diameter drill laterally from the interior of said drill guide locator member.

16. A device used to position and guide drills for forming bone passages during surgery, said device comprising:
   an arcuate support member;
   a locator probe member slidably positionable on said support member;
   a probe locking mechanism on said locator probe member for securing said probe member to said support member;
   said support member having first teeth means thereon and said probe locking mechanism having second teeth means which mate with said first teeth means to securely hold said probe member in position on said support member when said probe locking mechanism is moved to its locked position; and
   said probe locking mechanism including a lockplate member carrying said second teeth means and having at least one biased element for slidably contacting said support member, said biased element resisting engagement between said first and second teeth means when said second locking mechanism is moved to its unlocked position.

17. The device of claim 16 wherein said probe locking mechanism further includes a threaded turn knob for selectively contacting said lockplate member to engage said first and second teeth means when rotated in a first direction and for disengaging said first and second teeth means when rotated in a second direction.

18. The device of claim 16 wherein said support member defines at least two smooth tracks extending along said first teeth means, and said lockplate member includes at least one biased element for contacting and travelling along each said track.

19. The device of claim 18 wherein said probe locking mechanism further includes a threaded turn knob for selectively contacting said lockplate member to engage said first and second teeth means when rotated in a first direction and for disengaging said first and second teeth means when rotated in a second direction.

20. The device of claim 19 wherein said locator probe member includes a low-friction glide member for slidably contacting said support member to assist adjustment in position of said locator probe.

21. The device of claim 20 wherein said support member defines said first teeth means on a first surface and further defines a channel along a second surface, said channel having a barrier at each end, and said glide member extends into and travels along said channel between said barriers to prevent inadvertent removal of said locator probe member from said support member.

22. A device used to position and guide drills for forming bone passages during surgery, said device comprising:
a support member;
a drill guide locator member positioned on said support member; and
a first locking mechanism on said drill guide locator member for securing a drill sleeve member therein, said first locking mechanism having an inclined surface and a biased plunger member, and further including a manually actuable housing member slidably mounted on said drill guide locator member and carrying one of said inclined surface and said biased plunger member, the other of said inclined surface and said biased plunger member being separately mounted on said drill guide locator member, whereby actuation of said housing member moves said inclined surface relative to said biased plunger member.

23. The device of claim 22 wherein said housing member carries said inclined surface, and actuation in a first direction drives said biased plunger member into locking contact with the drill sleeve member to secure it in place, and wherein subsequent actuation of said housing member in a second, opposite direction enables said biased plunger member to withdraw from the drill sleeve member.

24. The device of claim 23 further including biased retention means, carried by said drill guide locator member, for releasably holding the drill sleeve member in place when said biased plunger member is withdrawn from locking contact with the drill sleeve member.

25. The device of claim 24 wherein said biased retention means includes a ball plunger member disposed in said drill guide locator member and having a biased ball means for slidably contacting the drill sleeve member, said biased ball means releasably retaining the drill sleeve member in place.

26. The device of claim 25 wherein said drill guide locator member defines a slit extending along its length for removing a narrow-diameter drill laterally from the interior of said drill guide locator member.

27. The device of claim 23 wherein said biased plunger member includes:
a plunger pin having a head at a first end for contacting said inclined surface and having a shaft at a second end;
a pin housing having an opening at a first end for receiving said plunger pins shaft and having a second end for contacting the drill sleeve member; and
spring washer means for providing compliance between said plunger pin and said pin housing.

* * * * *